United States Patent

Murphy-Chutorian et al.

[19]

[11] Patent Number: 6,001,091
[45] Date of Patent: Dec. 14, 1999

[54] REVASCULARIZATION WITH HEART PACING

[75] Inventors: Douglas R. Murphy-Chutorian, Palo Alto; Richard L. Mueller, Byron, both of Calif.

[73] Assignee: Eclipse Surgical Technologies, Inc., Sunnyvale, Calif.

[21] Appl. No.: 08/793,000

[22] Filed: Feb. 3, 1997

[51] Int. Cl.$^6$ .................................................. A61B 17/36
[52] U.S. Cl. ................................. 606/1; 606/12; 607/9
[58] Field of Search .............................. 606/1, 7, 15, 19, 606/14, 12; 607/9, 10, 33

[56] References Cited

U.S. PATENT DOCUMENTS

| | | |
|---|---|---|
| 4,418,688 | 12/1983 | Loeb . |
| 4,448,188 | 5/1984 | Loeb . |
| 4,453,547 | 6/1984 | Castel et al. ............................ 128/421 |
| 4,538,613 | 9/1985 | Rosenberg . |
| 4,641,650 | 2/1987 | Mok . |
| 4,641,912 | 2/1987 | Goldenberg . |
| 4,648,892 | 3/1987 | Kittrell et al. . |
| 4,654,024 | 3/1987 | Crittenden et al. . |
| 4,658,817 | 4/1987 | Hardy . |
| 4,669,467 | 6/1987 | Willett et al. . |
| 4,676,231 | 6/1987 | Hisazumi et al. . |
| 4,788,975 | 12/1988 | Shturman et al. ............................ 606/7 |
| 4,827,906 | 5/1989 | Robicsek et al. ............................ 600/17 |
| 5,125,926 | 6/1992 | Rudko et al. ............................ 606/19 |
| 5,672,170 | 9/1997 | Cho et al. ................................. 606/12 |

FOREIGN PATENT DOCUMENTS

| | | |
|---|---|---|
| 29610320 | 6/1996 | Germany . |
| WO 97/25101 | 7/1997 | WIPO . |

OTHER PUBLICATIONS

Rissel, U. et al., "A New 2–Channel Stimulation Device with Integrated Ablation–control Unit for the Diagnosis and Treatment of Cardiac Arrythmias," Biomed . Technik 33 (1988) pp. 18–25. English Translation of Biomed. Technik Article.

Abela et al., Effects of Carbon Dioxide, Nd–YAG, and Argon Laser Radiation on Coronary Atheromatous Plaques, The American Journal of Cardiology, vol. 50, Dec. 1982, pp. 1199–1205.

Abela et al., Laser Recanalization of Occluded Atherosclerotic Arteries In Vivo and In Vitro, Laboratory Investigation, Coronary Artery Disease, vol. 71, No. 2, Feb. 1985, pp. 403–411.

Anderson et al., Coaxial Laser Energy Delivery Using a Steerable Catheter in Canine Coronary Arteries, American Heart Journal, Jan. 1987, pp. 37–48.

H.T. Aretz et al., Intraluminal Ultrasound Guidance of Transverse Laser Coronary Atherectomy, SPIE vol. 1201 Optical Fibers in Medicine V (1990), pp. 68–78.

Bogen et al., Is Catheter Ablation on Target, The American Journal of Cardiology, vol. 60, Dec. 1, 1987, pp. 1387–1392.

Bommer et al., Laser Atrial Septostomy, American Heart Journal, Nov. 1983, pp. 1152–1156.

Bowker et al., Laser Assisted Coronary Angioplasty, European Heart Journal, ©1988, pp. 25–29.

Choy et al., Laser Coronary Angioplasty: Experience with 9 Cadaver Hearts, The American Journal of Cardiology, vol. 50, Dec. 1982, pp. 1209–1211.

(List continued on next page.)

*Primary Examiner*—Francis J. Jaworski
*Attorney, Agent, or Firm*—Wilson Sonsini Goodrich & Rosati

[57] ABSTRACT

An apparatus for treating a heart by stimulating revascularization of the heart or creating channels in the heart, the apparatus comprising an artificial energy source for causing a first created heartbeat and a revascularization device for creating a first revascularization event in the heart, the revascularization device being controllable to provide a first revascularization event to occur at a selected time in relation to the first created heartbeat.

41 Claims, 6 Drawing Sheets

OTHER PUBLICATIONS

Choy et al., Transluminal Laser Catheter Angioplasty, The American Journal of Cardiology, vol. 50, Dec. 1982, pp. 1206–1208.

Cox et al., Laser Photoablation for the Treatment of Refractory Ventricular Tachycardia and Endocardial Fibroelastosis, The Annals of Thoracic Surgery, vol. 39, No. 3, Mar. 1985, pp. 199–200.

Davi et al., Continous Wave (CW) and Pulsed Laser Effects on Vascular Tissues and Occlusive Disease in Vitro, Lasers in Surgery and Medicine 5:239–250 © 1985 Alan R. Liss, Inc.

Desilets et al., A New Method of Percutaneous Catheterization, Radiology, 85, Jul, 1965, pp. 147–148.

Goda et al., Myocardial Revascularization by CO2 Laser, © 1987 S. Karger AG Basel, Eur. surg. Res. 19;pp. 113–117.

Grundfest et al., Laser Ablation of Human Atherosclerotic Plaque Without Adjacent Tissue Injury, Laser Angioplasty: Morphologic Studies, JACC, Apr. 1985, pp. 929–933.

Hardy et al., Regional Myocardial Blood Flow and Cardiac Mechanics in Dog Hearts with CO2 Laser–induced Intramyocardial Revascularization, Basic Research in Cardiology, vol. 85, No. 2, 1990, pp. 179–197.

Isner et al., Identification of Photoproducts Liberated by In Vitro Argon Laser Irradiation of Atherosclerotic Plaque, Calcified Cardiac Valves and Myocardium, The American Journal of Cardiology, Apr. 1985, pp. 1192–1196.

Isner et al., Laser–Assisted Debridement of Aortic Valve Calcium, American Heart Journal, Mar. 1985, pp. 448–452.

Isner et al., Laser–Assisted Endocardiectomy for Refractory Ventricular Tachyarrhythmias: Preliminary Intraoperative Experience, Clinical Cardiology vol. 10, Mar. 1987, pp. 201–204.

Isner, et al., Laser Myoplasty for Hypertrophic Cardiomyopathy, Jun. 1, 1984, The American Journal of Cardiology, vol. 53, pp. 1620–1625.

Isner et al., Laser Photoablation of Pathological Endocardium: In Vitro Findings Suggesting a New Approach to the Surgical Treatment of Refractory Arrhythmias and Restrictive Cardiomyopathy, The Annals of Thoracic Surgery, Vol. 39, No. 3, Mar. 1985, pp. 201–206.

Jeevanandam et al., Myocardial Revascularization by Laser––Induced Channels, Surgical Forum XLI, Oct. 1990, pp. 225–227.

Josephson et al., Endocardial Excision: A New Surgical Technique for the Treatment of Recurrent Ventricular Tachycardia, Circulation, vol. 60, No. 7, Dec. 1979, pp. 1430–1439.

Kjellstrom et al., The Use of Lasers in Vascular and Cardiac Surgery, Acta Chir Scand 153, 1987, pp. 493–499.

Lee et al., Effects of Laser Irradiation Delivered by Flexible Fiberoptic System on the Left Ventricular Internal Myocardium, Sep., 1983, American Heart Journal, pp. 587–590.

Lee et al., Laser–Dissolution of Coronary Atherosclerotic Obstruction, American Heart Journal, Dec. 1981, pp. 1074–1075.

Lee et al., Potential Complications of Coronary Laser Angioplasty, American Heart Journal, Dec. 1984, pp. 1577–1579.

Lee et al., Transcatheter Ablation: Comparison between Laser Photoablation and Electrode Shock Ablation in the Dog, Mar. 1985, Laboratory Investigation, Laser Photoablation, vol. 71, pp. 579–586.

Masayoshi et al., Current Problems in Coronary Artery Surgery: New Methods for Myocardial Revascularization and Vascular Anastomosis, Jan., 1960, pp. 1203–1207.

Mirhoseiniet al., Clinical and Histological Evaluation of Laser Myocardial Revascularization, Journal of Clinical Laser Medicine & Surgery, Jun. 1990, pp. 73–78.

Mirhoseini et al., Clinical Report: Laser Myocardial Revascularization, © Alan R. Liss, Inc., Lasers in Surgery and Medicine 6:459–461 (1986).

Mirhoseini, Laser Applications in Thoracic and Cardiovascular Surgery, Medical Instrumentation, vol. 17, No. 6, 11–12, 1983, © 1983 Association for the Advancement of Medical Instrumentation.

Mirhoseini, Laser Revascularization of the Heart, New Frontiers in Laser Medicine and Surgery, ISBN Elsevier Science Publishing Co., pp. 296–303.

Mirhoseini et al., Lasers in Cardiothoracic Surgery, Chapter 21, pp. 216–232.

Mirhoseini et al., Myocardial Revascularization by Laser: A Clinical Report, © 1983 Alan R. Liss, Inc., Lasers in Surgery and Medicine 3:241–245.

Mirhoseini et al., New Concepts in Revascularization of the Myocardium, The Annals of Thoracic Surgery, vol. 45, No. 4, Apr. 1988, pp. 415–420.

Mirhoseini et al., Revascularization of the Heart by Laser, Journal of Microsurgery, Jun. 1981, pp. 253–260.

Mirhoseini, Transventricular Revascularization by Laser, Lasers in Surgery and Medicine, 2:187–198(1982).

Okada et al., Alternative Method of Myocardial Revascularization by Laser: Experimental and Clinical Study, Kobe J. Medical Science 32, Oct. 1986, pp. 151–161.

Regna, Abstract of U.S. Patent Application No. 4,796,630; Filed: Jan. 10, 1989.

Riemenschneider et al., Laser Irradiation of Congenital Heart Disease: Potential for Palliation and Correction of Intracardiac and Intravascular Defects, American Heart Journal, Dec. 1983, pp. 1389–1393.

Saksena et al., Laser Ablation of Normal and Diseased Human Ventricle, Jul. 1986, American Heart Journal, pp. 52–60.

Selle et al., Successful Clinical Laser Ablation of Ventricular Tachycardia: A Promising New Therapeutic Method, Ann Thorac Surg, Oct. 1986, pp. 380–384.

Svenson et al., Neodymium: YAG Laser Photocoagulation: A Succussful New Map–Guided Technique for the Intraoperative Ablation of Ventricular Tachycardia, Therapy and Prevention–Laser Photocoagulation, vol. 76, No. 6, Dec. 1987, pp. 1319–1328.

van Gemert et al., Optical Properties of Human Blood Vessel Wall and Plaque, Lasers in Surgery and Medicine, vol. 5, 1985, pp. 235–237.

White, Angioscopy and Lasers in Cardiovascular Surgery: Current Applications and Future Prospects, Aust. N.Z., Surg. 1988, pp. 271–274.

Zeevi et al., The Use of Carbon Dioxide Fiberoptic Laser Catheter for Atrial Septostomy, American Heart Journal, Jul. 1988, pp. 117–122.

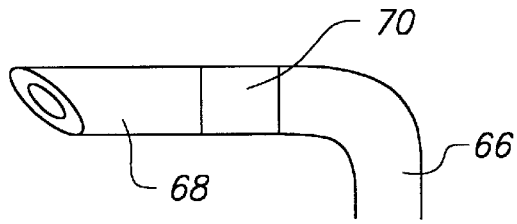
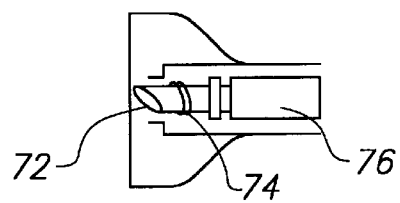
FIG. 4c      FIG. 4d
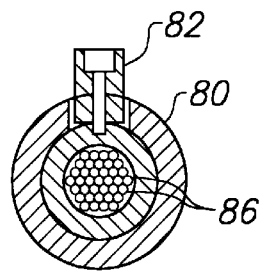
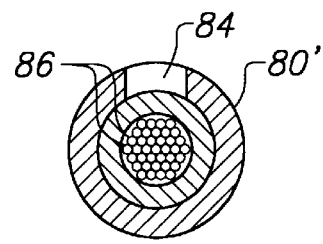
FIG. 5a      FIG. 5b
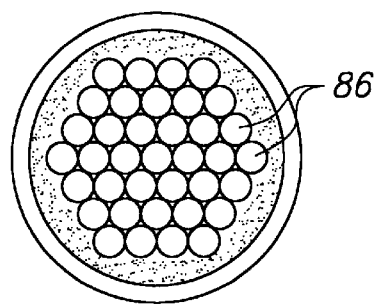
FIG. 5c
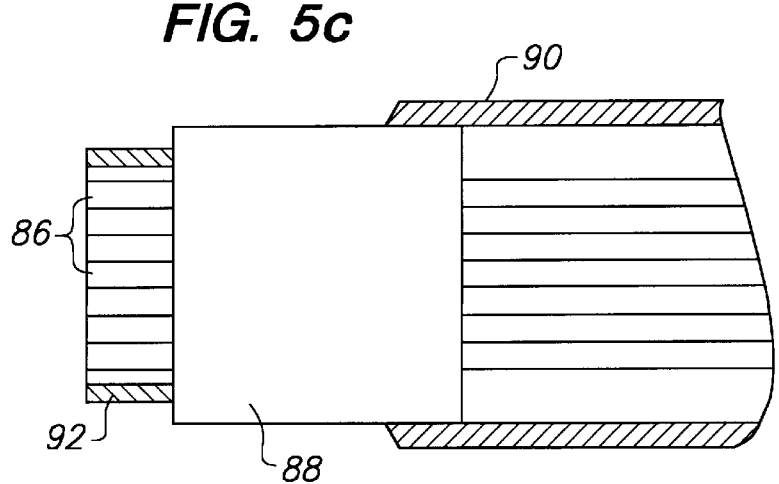
FIG. 5d

# REVASCULARIZATION WITH HEART PACING

CROSS-REFERENCE TO RELATED APPLICATIONS

The following applications are hereby incorporated herein by reference: U.S. Patent Application Entitled METHOD AND APPARATUS FOR CREATION OF DRUG DELIVERY AND/OR STIMULATION POCKETS IN THE MYOCARDIUM, application No. 08/773,788, Filed on Dec. 23, 1996, inventor(s): Mueller; U.S. Patent Application Entitled METHOD AND APPARATUS FOR MECHANICAL TRANSMYOCARDIAL REVASCULARIZATION OF THE HEART, application Ser. No. 08/713531, Filed on Sep. 13, 1996, inventor(s): Mueller and now U.S. Pat. No. 5,871,495; U.S. Patent Application Entitled METHOD FOR NON-SYNCHRONOUS LASER ASSISTED TRANSMYOCARDIAL REVASCULARIZATION, application Ser. No. 08/729325, filed on Oct. 15, 1996, inventor(s): Murphy-Chutorian and now U.S. Pat. No. 5,785,702; and U.S. Patent Application Entitled MINIMALLY INVASIVE METHOD FOR FORMING REVASCULARIZATION CHANNELS, application Ser. No. 08/794,733, inventor(s) Daniel et. al.

BACKGROUND OF THE INVENTION

1. Field of the Invention

This invention relates generally to a method and apparatus for revascularization of a heart, and more particularly to a method and apparatus for revascularization using heart pacing.

2. Description of Related Art

Heart disease is a significant health problem which has been the subject of substantial medical study. By-pass surgery has become commonplace, yet such surgery may only partially correct a diminished blood supply to heart muscle and may be unavailable to many patients, either because of the nature of the occlusions or the physical condition of the patient.

One promising alternative or adjunctive technique for treating such cases is known as transmyocardial revascularization (TMR). This technique was considered in the work of Dr. C. Beck in "the Development of a New Blood Supply to the Heart by Operation," *Annals of Surgery Annals of Surgery*, Vol. 102, No. 5 (11/35) pp. 801–813. The method was also studied in the work of Dr. M. Mirhoseini and M. Cayton, an example of which is found in "Lasers and Cardiothoracic Surgery" in *Lasers in General Surgery* (Williams and Williams, 1989) pp. 216–223. A device to perform TMR is described in Aita et al., U.S. Pat. No. 5,380,316, issued Jan. 10, 1995. In TMR generally the surgeon creates narrow channels in the heart at the surface of a ventricle of the heart. The surgeon generally uses a laser to create these channels either by accessing the endocardium through a percutaneous route or the epicardium through an incision in the chest wall. The pressure within the left ventricle during systole forces oxygenated blood into the channels and consequently oxygenates the ischemic myocardium of the left ventricle.

It is desirable to be able to control the time point within the cycle of heartbeats at which the heart is revascularized. A heart synchronized pulse laser system which operates on a beating heart between the R and T waves of the electrocardiogram (ECG) signal is described in U.S. Pat. No. 5,125,926 (Rudko).

An electrocardiogram signal may not always provide the most accurate indication of heart function. Further, the electrocardiogram signal is a passive indication of heart rate. It is not a method to control the rate at which the heart beats.

There is a need for an apparatus for stimulating revascularization of the heart or creating channels in the heart where the revascularization event caused by the revascularization device can occur at a selected time in relation to the heartbeat. There is a further need for an apparatus for treating a heart by stimulating revascularization of the heart or creating channels in the heart where the device can control the heartbeat rate. There is further need to reduce the number of cycles over which a laser must be fired to achieve the desired depth of channels in the heart.

SUMMARY OF THE INVENTION

Accordingly, an object of the invention is to provide an apparatus for stimulating revascularization of the beating heart or creating channels in the heart.

Further, an object of the invention is to provide an apparatus for stimulating revascularization of the heart or creating channels in the heart where the revascularization or creation of channels occurs at a time when the heart is less sensitive to external influences.

Another object of the invention is to provide an apparatus for stimulating revascularization of the heart or creating channels in the beating heart where the revascularization or creation of channels occurs when the beating heart is relatively still.

A further object is to reduce the number of cycles over which the laser must be fired.

Another object of the invention is to provide an apparatus for stimulating revascularization of the heart or creating channels in the heart where the revascularization event caused by the revascularization device can occur at a selected time in relation to the heartbeat.

Another object of the invention is to provide an apparatus for treating a heart by stimulating revascularization of the heart or creating channels in the heart where the device can control the heartbeat rate.

Another object of the invention is to help cause a stabilized beat to occur after laser firing to steer the heart back quickly to a regular pattern, interrupting a memory effect possible by continuing fibrillations.

These and other objects are achieved in an apparatus for treating a heart by stimulating revascularization of the heart. The apparatus includes an artificial energy source for causing a created heartbeat and a revascularization device for creating a revascularization event in the heart. The revascularization device is controllable to cause the revascularization event to occur at a selected time in relation to the created heartbeat.

In various embodiments, the selected time is fixed to cause the revascularization event to occur after depolarization and before repolarization of the heart, the selected time is fixed to cause the revascularization event to occur substantially simultaneously with the created heartbeat, or the selected time is variable. In another embodiment of the invention, the revascularization device is configured to cause multiple revascularization events in the heart.

The revascularization device may be a laser energy delivery device, a mechanical cutter, an ultrasound energy delivery device, or other device to make channels or to stimulate the heart. The artificial energy source for causing a created heartbeat may be a pacemaker or other device for causing heartbeats. In another embodiment of the invention, the artificial energy source for causing a created heartbeat is the revascularization device.

In one embodiment of the invention an apparatus is provided for controlling a revascularization device with a control circuit coupled to a revascularization device. The control circuit is configured to cause the revascularization device to create a revascularization event in the heart at a selected time relative to a created heartbeat. The created heartbeat is created by an artificial energy source.

In another embodiment of the invention a method is provided for treating a heart by stimulating revascularization of the heart or creating channels in the heart. A device is provided for introducing energy to the heart. Energy delivered from the device for introducing energy to the heart causes a created heartbeat. A revascularization event is created in the heart at a selected time in relation to the created heartbeat.

BRIEF DESCRIPTION OF THE FIGURES

FIG. 4c is a perspective view of a piercer with an electrode.

FIG. 4d is a cross sectional view of an electrically controllable mechanical cutter.

FIG. 5a is a cross sectional view of a catheter with fiber optic fibers.

FIG. 5b is a cross sectional view of a catheter with fiber optic fibers.

FIG. 5c is a cross sectional view of a catheter with fiber optic fibers.

FIG. 5d is a cross sectional view of a catheter with fiber optic fibers.

DETAILED DESCRIPTION

The apparatus and method of the present invention create channels or stimulation zones or both in the heart through a series of revascularization events. A revascularization device is used to create channels or stimulation zones in the heart. A revascularization device is one or more laser energy delivery devices (fired alone, simultaneously, or sequentially), a mechanical cutter, an ultrasound energy delivery device, or other device or devices for creating channels in heart tissue. A revascularization event is an action of the revascularization device as the device cuts, burns, lases, or otherwise creates or lengthens channels in the heart tissue. The channels or stimulation zones allow for improved bloodflow in heart tissue and/or help to stimulate regrowth of capillaries.

The apparatus and method of the present invention provide revascularization events to the heart at a specific time in the heartbeat cycle. The heart is paced. A pace signal starts a heartbeat cycle. A revascularization event is provided to the heart relative to the pace signal. By timing the revascularization event with respect to the pace signal, the revascularization event is provided at a selected time within the created heartbeat cycle.

The time within the cycle between the two created heartbeats at which the revascularization event occurs can be selected to provide an optimal time at which to cause a revascularization event to occur. The time delay can be selected so that the revascularization occurs when the heart is less sensitive to external stimuli, or when the heart is more quiet so as to reduce the risk to the patient and help achieve better revascularization. After the created heartbeat is created, a revascularization period begins and during the revascularization period a revascularization event is caused to occur.

An energy source, including but not limited to a pacemaker, is used to pace the heart and cause the heart to beat at a selected rate. The surgeon may enable the revascularization apparatus with a foot switch. A control circuit receives input from the surgeon's foot switch. The control circuit causes the revascularization device to start a revascularization event at a time relative to the time the energy source causes the heart to beat. Among the advantages of pacing the heart while performing revascularization is that the surgeon can control the rate of the heart and not have to rely exclusively on the natural rhythms of a possibly compromised or sick heart.

Figure 1:
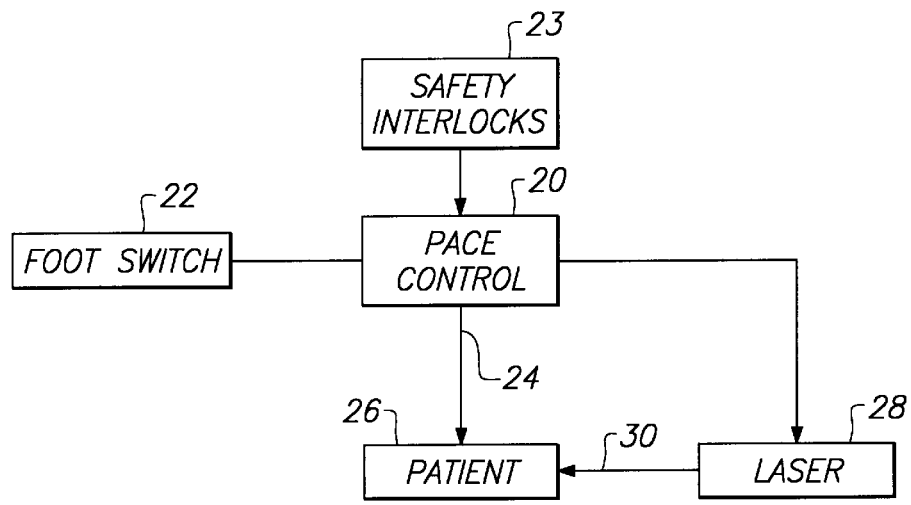
FIG. 1 is a block diagram of a system for performing transmyocardial revascularization.

Referring now to FIG. 1, the surgeon enables the apparatus through footswitch 22. Pace control block 20 receives a signal from safety interlocks 23 and footswitch 22, which is operated by the surgeon. Pace control block 20 outputs signals to pacing leads 24 which provide a pacing signal to patient 26. The pacing signal causes a created heartbeat and causes the patient's heart to beat at the pace rate provided by pace control block 20. Pace control block 20 sends a signal to a laser 28 to cause laser 28 to provide laser energy through optical fiber 30 to the patient's heart at a selected time in relation to the created heartbeat. The energy provided through optical fiber 30 is used to revascularize or to create channels in the heart of patient 26.

Figure 2:
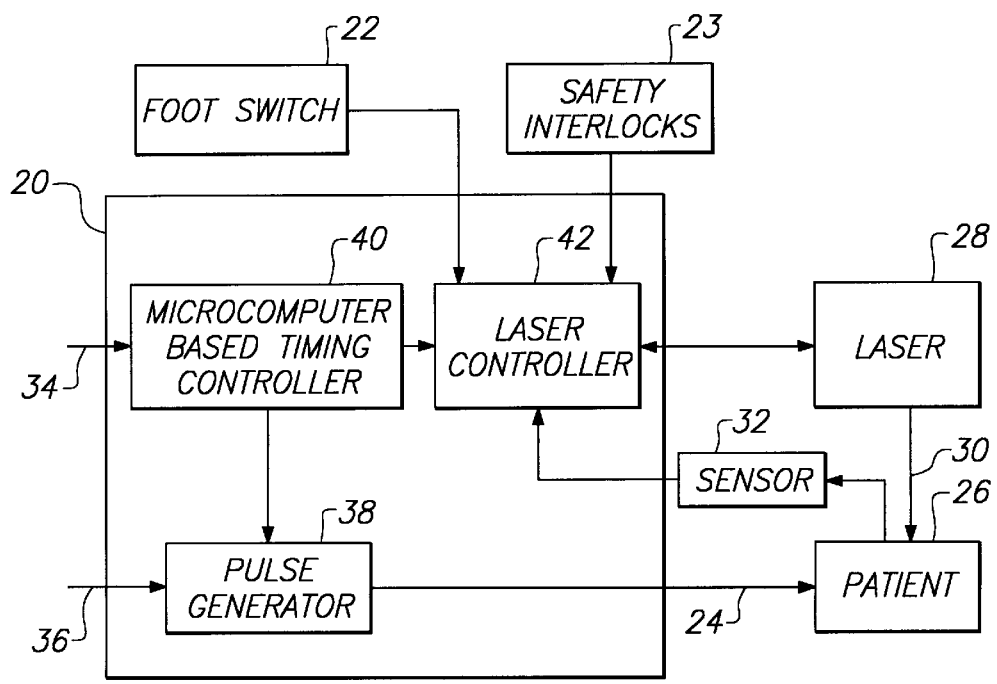
FIG. 2 is a block diagram of a system for performing transmyocardial revascularization including a block diagram of a pulse generator.

Referring now to FIG. 2, pace control block 20 includes microcomputer based timing controller 40, pulse generator 38, and laser controller 42. Desired rate 34 is coupled to a microcomputer based timing controller 40 and controls the rate at which pulse generator 38 provides pacing signals to patient 26 via pacing leads 24. Desired current 36 is coupled to pulse generator 38 and controls the level of current that is provided to patient via pacing leads 24 in order to pace the patient's heart. The output of microcomputer based timing controller 40 provides timing signals to laser controller 42. The timing signals cause the revascularization event to occur at the selected time relative to the created heartbeat created by pulse generator 38. The input of sensor 32 is coupled to patient 26. Sensor 32 is not necessary for the operation of the system and is therefore optional. The optional signal from sensor 32 is a heartbeat indicator signal. The heartbeat indicator signal indicates whether the patient's heart is beating. The output of footswitch 22, safety interlocks 23, timing signals from microcomputer based timing controller 40, and the output of sensor 32 are combined in laser controller 42 to provide a laser active signal to laser 28. Thus, a signal is provided only when all of the following occur: the surgeon has enabled the system via the footswitch, the safety interlocks are enabled, the optional heartbeat indicator indicates that the heart is beating, and a signal is provided to fire the laser from the output of microcomputer based timing controller 40. Laser 28 provides laser energy over optical fiber 30 in order to create a revascularization event in the heart to stimulate revascularization of the heart of patient 26 or to create channels in the heart to improve blood flow.

In an alternative embodiment signals from foot switch 22 or from sensor 32 or both could be input into microcomputer based timing controller 40 instead of into laser controller 42. In such a configuration, microcomputer based timing controller 40 would then provide appropriate signals to laser controller 42 partially in response to signals from foot switch 22 or from sensor 32. Also, instead of providing control to pulse generator 38, microcomputer based timing controller 40 could receive information from pulse generator 38 regarding the timing of pulses and then microcomputer based timing controller 40 would provide control to laser controller 42 in response to the timing of pulses.

Microcomputer based timing controller 40 is a microcomputer that runs a set of software instructions recorded in a memory. Alternatively, integrated circuit logic may be used to perform the function of microcomputer based timing controller 40.

Pulse generator 38 provides the pacing signal to the patient's heart or to another location on the patient's body in order to pace the patient's heart via pacing leads 24. Pulse generator 38 may be a heart pacemaker such a modified model 540 External Pulse Generator, SeaMED Corp., Redmond, Wash. The pacemaker is modified such that it generates a pulse to the pacing leads when it receives an external logic signal. Alternatively, pulse generator 38 is any artificial energy source capable of causing the heart to beat.

The pace rate is determined by desired rate 34 and can be set by the operator. The rate of pace unit 38 is optimally set to a rate faster than the normal heartbeat rate. Heartbeat rate can be determined manually or by sensor 32 or by any other method or heartbeat rate measurement. If the signal from sensor 32 is provided to microcomputer based timing controller 40, then controller 40 optionally uses the output information from the sensor 32 to determine the patient's heart rate before the patient's heart is paced and optionally calculates and applies a pace rate faster than the unpaced heartbeat rate. If microcomputer based timing controller 40 is configured to automatically deliver a pace rate faster than the unpaced heartbeat rate, the automatically determined pace rate can be manually overridden by the operator. Sensor 32 can be an electrocardiogram unit, a pressure transducer, a Doppler effect heartbeat rate sensor, or other sensor to measure heart function.

In a preferred embodiment laser 28 is a holmium laser available as an Eclipse 4000™ holmium laser from Eclipse Surgical Technologies, Inc., Sunnyvale, Calif. Other types of medical lasers may also be used, for example, an excimer laser, a $CO_2$ laser, an Argon laser, a Nd-yag laser, an erbium laser, or a diode laser. A single laser may be used, or multiple lasers or multiple fibers from a single laser can be used in order to cause more revascularization to occur at one time. For a discussion of tuning of a laser for revascularization, see U.S. Pat. No. 5,785,702 entitled Method for Non-Synchronous Laser Assisted Transmyocardial Revascularization, which is incorporated herein by reference. As an alternative to a laser revascularization device, another revascularization device such as a mechanical cutter or an ultrasound energy delivery device may be used in order to create channels in the heart or to revascularize the heart. The revascularization device can be coupled to a catheter for percutaneous and minimally invasive surgery (MIS) approaches. Alternatively, the revascularization device can be used directly in open heart surgery. If the revascularization device is coupled to a catheter, it can be introduced percutaneously and moved into the heart through the vasculature.

Microcomputer based timing controller 40 can be configured so that the time delay from the pace signal created by the pulse generator 38 to the time of the revascularization event is a fixed time. A 120 ms delay is generated as a default. Alternatively, the microcomputer based timing controller 40 can be configured so that the time delay from the signal from the pulse generator 38 to the revascularization event is a variable time. The revascularization time may be variable so that it is shorter when revascularization is taking place closer to the sinus node and longer when revascularization is taking place further away. The varying delay may be controlled as set by the operator or automatically varied. The time delay can be set to cause the revascularization event to occur at a chosen point within the created heartbeat cycle. This chosen point in time can be chosen so as to cause the least amount of interference or irritation to the heart. The point in time may be chosen to be the point at which the heart is relatively quiet electrically. This point may also be chosen to be the point at which the heart is mechanically still. In particular, the revascularization event may be caused to occur after a depolarization of the heart and before a repolarization of the heart. The revascularization event may be caused to occur after an R wave and before a T wave produced by the heart. Microprocessor based timing controller 40 can be configured to have a fixed or variable number of pulses, and variable or fixed pulse repetitive interval. Microcomputer based timing controller 40 controls the frequency and duration of laser outputs and the resulting revascularization events and thus has an effect on the amount of revascularization or on the depth of the channel created in the heart during the revascularization event.

In an alternative embodiment, microcomputer based timing controller 40 is configured to cause laser 28 to deliver multiple laser pulses for each pace signal which are used to help create a greater depth of revascularization per heartbeat or to create a series of stimulation pockets connected by narrow channels. If multiple lasers or multiple fibers from one laser are used, then multiple channels can also be created simultaneously. In another embodiment, microcomputer based timing controller 40 can be configured to cause laser 28 to deliver revascularization events to the patient's heart at a time in the heartbeat cycle so that the revascularization event also causes a heartbeat. After a beat is created by a laser pulse, another laser pulse is delivered to create a revascularization event. In this mode of operation when footswitch 22 is activated, the pulse generator 38 is disabled and one or more revascularization events are delivered to patient's 26 heart during a time that the pacemaker signal would have been delivered. In this manner the laser can be used to pace the patient's heart.

Optical fiber 30 may be introduced into patient 26 via a catheter in a percutaneous procedure. Alternatively, optical fiber 30 can be provided to patient 26 through open heart surgery or MIS techniques. A laser energy delivery device provides the energy from the laser 28 to the heart of patient 26. In FIG. 2 the laser energy delivery device is shown as an optical fiber. Other forms of laser energy delivery devices could also be used to provide energy from a laser to the heart of patient 26.

Figure 3A:
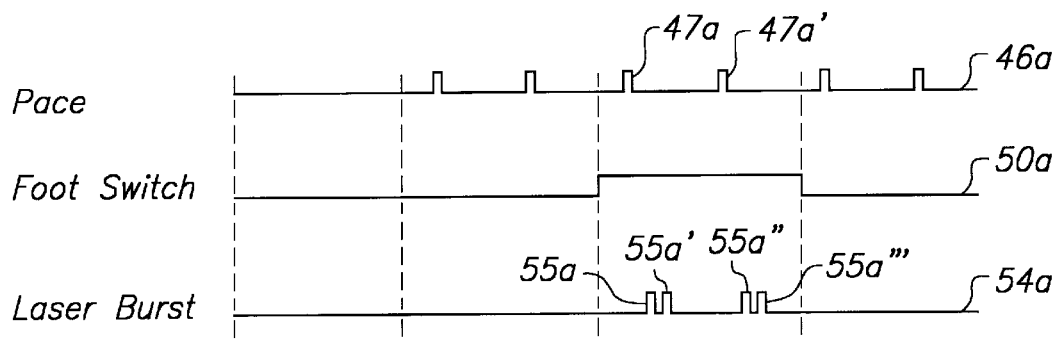
FIG. 3a is a timing diagram for revascularization with heart pacing including a foot switch signal.

FIG. 3a includes pace signal 46a, footswitch signal 50a, and a laser burst signal 54a. Signal 55a occurs after pace signal 46a is active at 47a. Thus, a revascularization occurs after the heart is paced. As shown, laser burst 55a and 55a' occur only when foot switch signal 50a is active. Laser burst signals 55a and 55a' occur after pace signal 47a but before pace signal 47a'. Laser burst signals 55a" and 55a'" occur after the pace signal 47a'.

By selecting the time delay between a pace signal 47a and a revascularization event 54a, the revascularization event can be caused to occur at a selected time relative to the heartbeat. This time is selected in order to reduce the possible negative effects on the heart because of irritation from the revascularization event such as causing arrhythmias or other disturbance to the heart. In one embodiment the revascularization event occurs when the heart is electrically quiet or when the heart is more still mechanically than at other times relative to the heartbeat. Footswitch signal 50a is a signal that is provided by the footswitch controlled by the surgeon. The time delay from the pace signal 47a to the revascularization event 55a can be set at a fixed value as optimally chosen to reduce problems with the heart. Alternatively, this time delay can be variable.

Figure 3B:
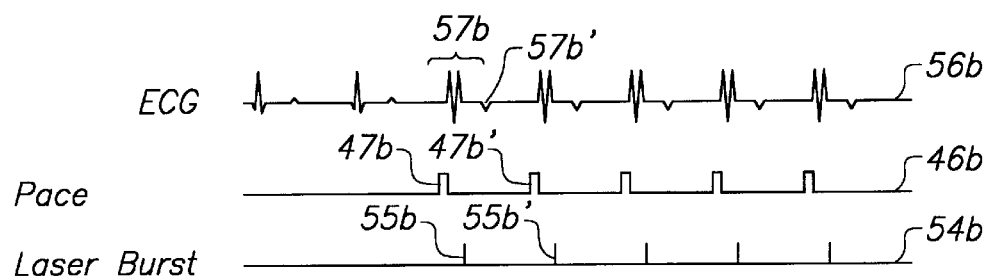
FIG. 3b is a timing diagram for revascularization with heart pacing.

As shown in FIG. 3b, the time delay between the pace signal 47b and laser burst signal 55b is set so that the laser burst signal 55b occurs between the R wave 57b and the T wave 57b'. The electrocardiogram signal 57b is shown for illustrative purposes and is not used to control the time at which the laser burst occurs. The heart is paced at a rate faster than the unpaced heartbeat rate. As shown on signal 56b, the time between heartbeats is greater prior to signal 47b than after signal 47b. The rate of the paced heart is faster than the rate of the unpaced heart in order to allow the pace signal 46b to control the heart. The signal from an electrocardiogram or other sensor can be used to calculate a pace rate faster than the normal unpaced heart rate and provide the pace signal 46b at this pace rate. If the heart during revascularization goes into a fast or chaotic rhythm the operator may change the rate of pacing in order to attempt to regulate the heart rate and return the heart rate to a rate closer to the normal heart rate.

Figure 3C:
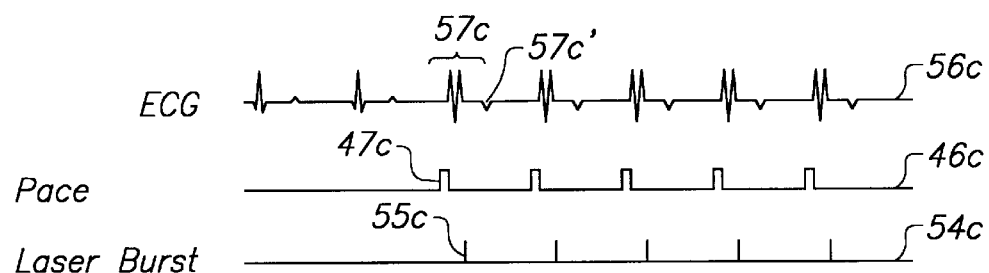
FIG. 3c is a timing diagram for revascularization with heart pacing.

FIG. 3c includes electrocardiogram signal 56c, pace signal 46c, and laser burst signal 54c. Electrocardiogram signal 56c is not used to control the laser burst. As can be seen in the FIG. 3c, the heart beats in response to pace signal 46c as seen in electrocardiogram signal 56c which indicates heartbeats. The time delay between pace signal 47c and laser burst signal 55c is such that the laser burst occurs during the heartbeat as represented by signal 57c. Alternatively, the laser burst can be timed to occur simultaneously or substantially simultaneously with the pacing signal 47c.

Figure 3D:
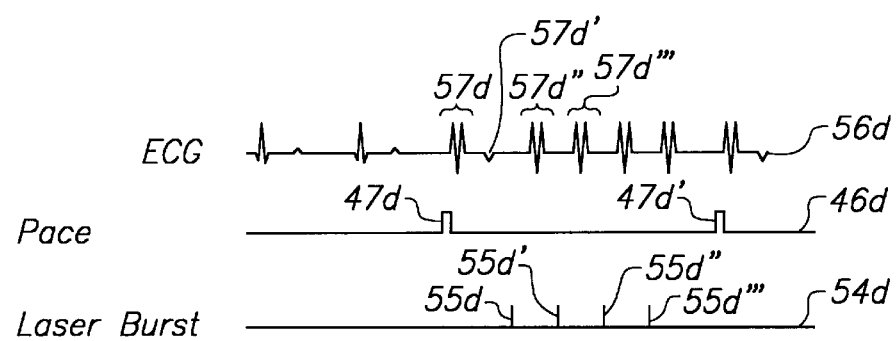
FIG. 3d is a timing diagram for revascularization with heart pacing including laser pulses that cause heartbeats.

FIG. 3d is a timing diagram for revascularization with heart pacing including laser pulses that cause heartbeats. Electrocardiogram signal 56d is not used to control the laser burst or the periods at which they occur. As seen in the FIG. 3d, the heart rate before pace signal 47d is slower than the heart rate after pace signal 47d. Between the pace signal 47d and 47d' the heart beats in response to the laser bursts 55d, 55d', 55d", and 55d'". As shown in FIG. 3d the revascularization events or the laser bursts occur at a time at which they cause the heart to beat.

Figure 3E:
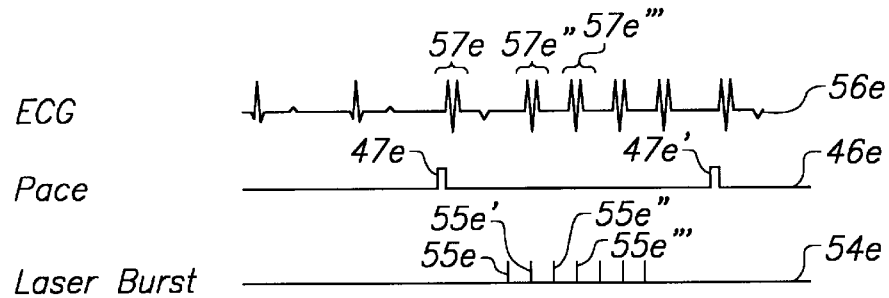
FIG. 3e is a timing diagram for revascularization with heart pacing including laser pulses that cause heartbeats and including multiple laser pulses per heartbeat.

FIG. 3e includes electrocardiogram signal 56e, pace signal 46e, and laser burst signal 54e. There are no signals from the pacer between signal 47e and 47e'. Laser 28 is used to pace the heart during this period. Further, multiple pulses of the laser occur for each heartbeat. For example, after the laser pulse 55e which causes the heart to beat as demonstrated by electrocardiogram signal 57e", a second laser pulse occurs at signal 55e', which does not cause the heart to beat in response.

Figure 3F:
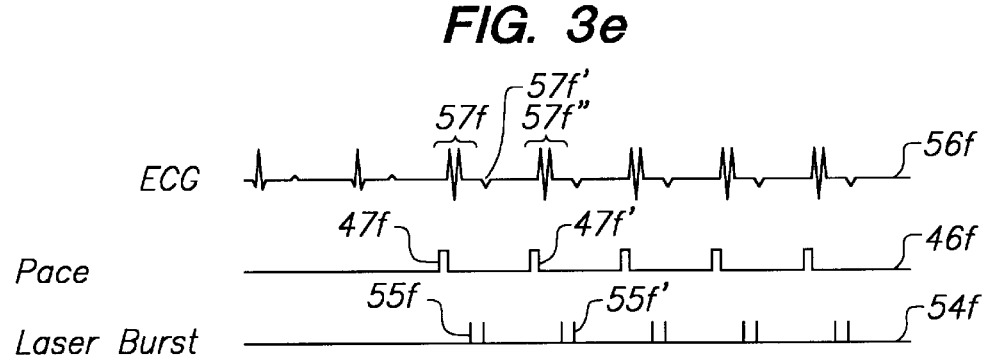
FIG. 3f is a timing diagram for revascularization with heart pacing including multiple laser pulses per heartbeat.

FIG. 3f illustrates revascularization with heart pacing including multiple laser pulses per heartbeat cycle. FIG. 3f includes electrocardiogram signal 56f, pace signal 46f, and laser burst signal 54f. Electrocardiogram signal 56f or signal from another type of sensor (e.g. pressure sensor) can be used to observe whether the heart is beating efficiently and to disable the laser if the heart is not beating. Laser bursts 55f and 55f' occur after pace signal 47f and after R wave 57f and before T wave 57f'. Multiple laser bursts 55f and 55f' are provided in order to allow for possibly greater depth of revascularization per heartbeat cycle or to create stimulation zones with or without connecting channels. The rate at which the heart is paced is faster than the unpaced rate of the heart. As seen in FIG. 3f, the time between heartbeat signals on the electrocardiogram signal 56f is greater before first pace signal 47f than the time between heartbeat signals after pace signal 47f. It may be desirable to cause a revascularization event to occur after a depolarization of the heart and before a repolarization of the heart.

Figure 3G:
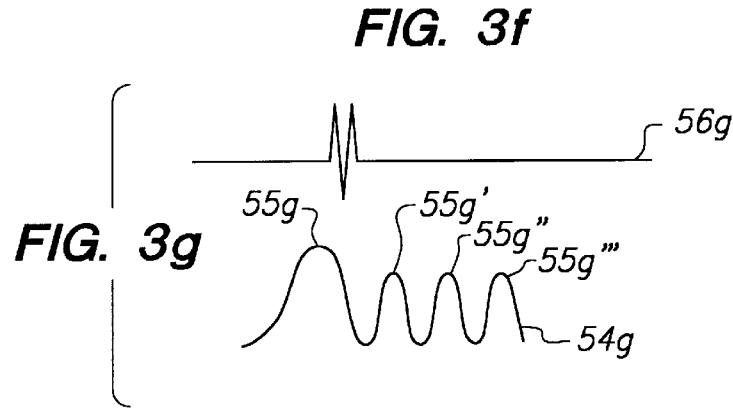
FIG. 3g is a timing diagram for revascularization with heart pacing including multiple laser pulses of different intensities.

As shown in FIG. 3g, first pulse 55g is stronger than subsequent pulses 55g, 55g', 55g", and 55g'" in order to allow the first pulse to pace the heart and subsequent pulses to be used to revascularize or create a channel into the heart. The heart beats in response to first laser pulse 55g. Alternatively, first laser pulse 55g can be smaller than the subsequent ones so that the first pulse is large enough to pace and subsequent ones are larger for greater revascularization.

The apparatus and method described above may be used in a percutaneous procedure, in a minimally evasive surgery (MIS) procedure, or other surgical procedure. In a percutaneous procedure, a catheter is introduced into the vasculature and revascularization events are created using the catheter. In a MIS procedure, apparatus to perform revascularization is introduced into the body through a port, an opening that is small relative to the opening used in typical heart surgery. Other surgical methods can be used with paced revascularization described.

Figure 4A:
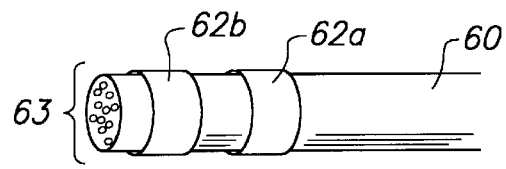
FIG. 4a is a perspective view of a fiber optic catheter with pacing leads.

As illustrated in FIG. 4a electrode 62a and electrode 62b are mounted on catheter 60 near the distal end of catheter 60. Fiber optic fibers 63 are located in the interior of catheter 60 and extend to the distal end thereof in order to provide laser energy to the heart for creating channels and revascularization. Electrodes 62a and 62b provide artificial energy that causes a created heartbeat in the heart. This artificial energy is a pacing signal. Electrodes 62*a* and 62*b* are located near the distal end of catheter 60 in order to provide a pacing signal close to the location of revascularization. Catheter 60 can be used for ventricular pacing and artrial pacing by placing the electrodes 62*a* and 62*b* on a location and on catheter 60 so that they are in either the atrium or ventricle as chosen. Electrodes 62*a* and 62*b* can be used to pace directly into those locations of the heart. A sensor such as a pressure transducer can also be coupled to the catheter 60 along with the pacing electrodes 62*a* and 62*b*.

Figure 4B:
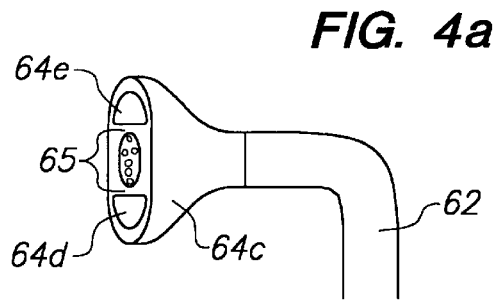
FIG. 4b is a perspective view of a fiber optic laser energy delivery device handpiece with pacing leads.

FIG. 4*b* is a perspective view of a fiber optic laser energy delivery device handpiece 62 with pacing leads as could be used for surgical paced revascularization or, with modifications, in MIS applications. Handpiece 62 is for controllably advancing a fiber. Such a handpiece is available under the name Sologrip™ from Eclipse Surgical Technologies, Sunnyvale, Calif. FIG. 4*b* shows electrode end 64*c*, electrode 64*e*, electrode 64*d*, and fiber optic fibers 65. The electrode 64*d* and electrode 64*e* are located at the distal end of the laser energy delivery device handpiece 62 and extend though the laser energy delivery device handpiece 62. The location of the electrodes 64*d* and 64*e* provides the pacing signal close to the location of revascularization.

FIG. 4*c* shows a perspective view of a piercer 66 with an electrode 68. Electrode 68 is located at the distal end of piercer 66, and insulator 70 is located around the distal end of the piercer 66. The piercer can be used for revascularization. Piercer 66 may be a hollow needle, thereby allowing the laser fiber optic device to extend therethrough. Alternatively, piercer 66 may be angled fibers. Piercing, particularly when performing TMR from the epicardial surface is helpful to reduce acute bleeding, to anchor the device to the beating heart, and to reduce adhesions between the epicardium and the pericardium.

FIG. 4*d* is a cross sectional view of an electrically controllable mechanical cutter. The mechanical cutter includes a piercer 72, a spring 74, and a solenoid 76. Piercer 72 is driven by spring 74 as controlled electrically by solenoid 76. This construction allows this mechanical piercer 72 to be electronically controlled. The time of the piercing can be set relative to the pace signal of the heart. Alternatively, the piercing can be timed so as to cause the heart to beat.

Referring now to FIGS. 5*a* to 5*d*, embodiments of a catheter with fiber optics 86 are illustrated. The FIGS. 5*a* to 5*d* show fiber bundles; however, it is appreciated that single fibers, waveguides, lenses used with fibers, or lenses in articulated arms could also be used. In FIG. 5*a* the fibers 86 are surrounded by handle 80. A slot 82 is configured to receive a control knob. FIG. 5*b* shows a handle 80' and a slot 84 through handle 80'. Slot 84 may be used for a control knob or control block to slide fibers 86 through the body of handle 80. FIG. 5*c* shows glass fibers 86 in a bundle of fibers. Alternatively, a single fiber, wave guide, or CO$_2$ laser handpiece may be used. FIG. 5*d* shows a protective sheath 90 over a bundle of fibers including fibers 86. A marker 88 is positioned around fibers 86. Marker 88 is comprised of tantalum or similar material. Epoxy 92 holds fibers 86 together.

In each of the paced revascularization procedures (percutaneous, MIS, and other surgical procedures), any pacemaker lead placement method can be used. For example, pacemaker leads may be placed on a catheter, as described above. A pacing lead can be introduced percutaneously by introducing pacing leads into the p. saphenous vein and through the right femoral vein (medial to the right femoral artery), then threading the lead up through the inferior vena cava and into the right ventricle, and letting the lead lay on the right ventricle during the procedure. A pacing lead may be attached directly to the heart during surgery. A pacing lead can be introduced in a MIS approach wherein the pacing wire is placed directly on the epicardium through a port and is attached to the right ventricle with a small suture needle during the procedure. As indicated above, as with the other approaches to introducing pacing leads, the MIS approach of pacing lead placement can also be used with any of the paced revascularization procedures.

Figures 6, 7:
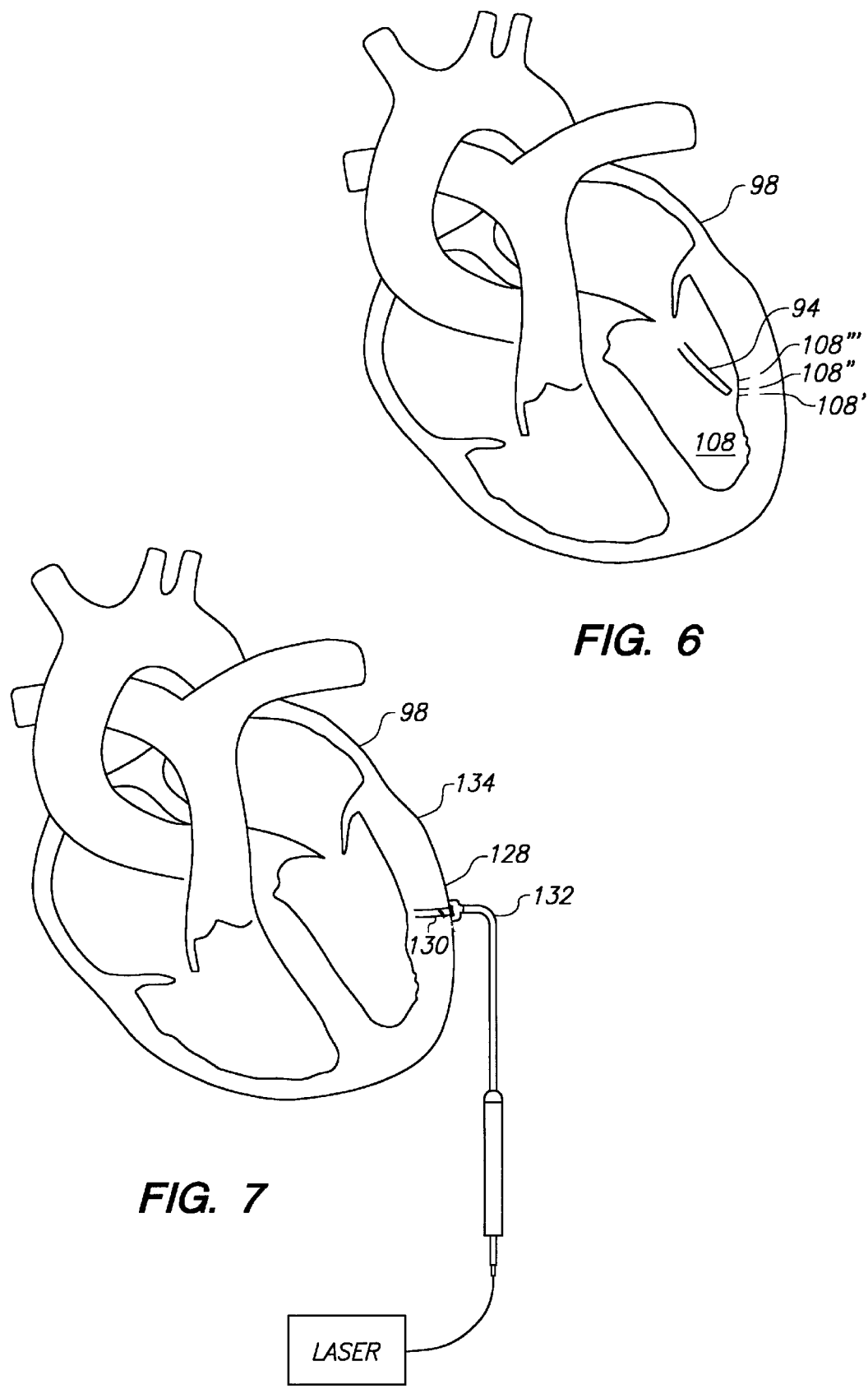
FIG. 6 is a cross sectional view of a heart with revascularization channels created in a percutaneous procedure.
FIG. 7 is a cross sectional view of a heart with a revascularization channel created in a surgical procedure.

As shown in FIG. 6, paced revascularization can be performed percutaneously. A revascularization device 94 is introduced percutaneously into the vasculature and moved into the heart 98. Revascularization device 94 is used to create channels 108', 108", and 108''' in heart 98. Here the channels are shown in the left ventricle 108. The revascularization channels 108', 108", and 108''' help to improve blood flow to the heart and help to stimulate the regrowth of capillaries. Channels extend from the ventricle partway through the myocardium.

FIG. 7 shows surgical paced revascularization. Laser energy delivery device 132 is introduced surgically into the body and creates channel 130 through the epicardium 128. Minimally invasive surgery (MIS) can also be used for paced revascularization and can be used to create a channel 130 in the epicardium 128. Pacing leads may be placed approximately at point 134 on heart 98. Alternatively, any other method of pacing lead placement can be used, such as placing leads in the ventricle of the heart or on the laser energy delivery device 132.

Figure 8A:
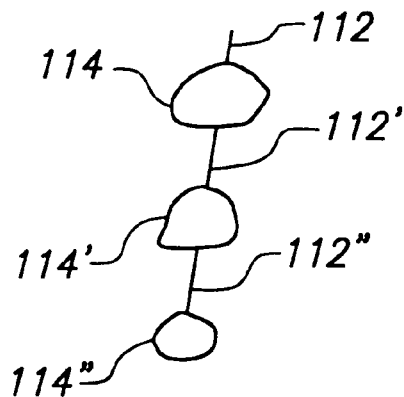
FIG. 8a is a view of channels and pockets created in heart tissue.
Figure 8B:
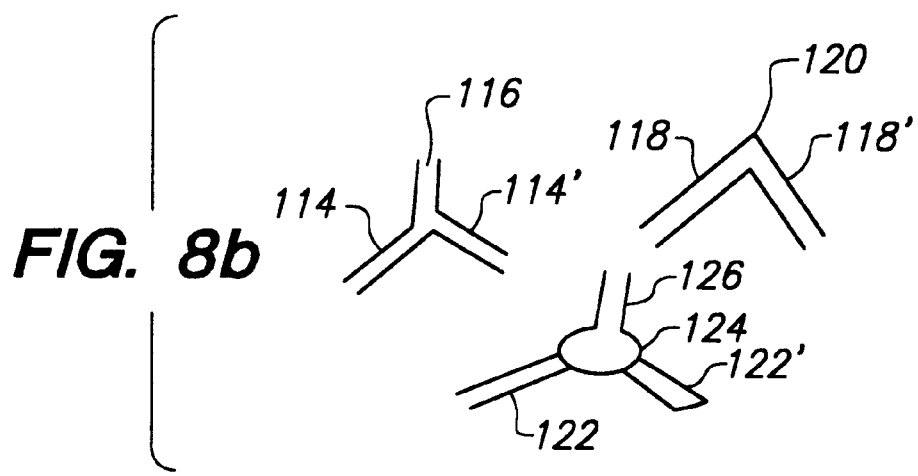
FIG. 8b is a view of multiple legs created from channels in heart tissue.

As shown in FIG. 8*a*, narrow stimulation zones created as narrow channels 112, 112', and 112" can be produced in heart tissue. Narrow channels 112, 112', and 112" can be created between created pockets 114, 114', and 114" in heart tissue. Narrow channels may close and pockets may remain open. As shown in FIG. 8*b*, channels may also have multiple legs 114 and 114' extending from a single entry 116. FIG. 8*b* also shows legs 118 and 118' extending from entry 120. Multiple legs 122 and 122' may extend from a pocket 124, which is created from a single entry 126. Some of the legs may not extend through the myocardium. Such legs that do not extend through the myocardium can be referred to as blind channels and can be used for depositing drugs directly into heart tissue.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for treating a heart, the apparatus comprising:
    a revascularization device for creating a first revascularization event in the heart; and
    a control circuit, coupled to the revascularization device, that causes
    the revascularization device to cause a first created heartbeat and
    the revascularization device to create the first revascularization event in the heart at a selected time in relation to the first created heartbeat.

2. The apparatus of claim 1, wherein the selected time is fixed.

3. The apparatus of claim 1, wherein the selected time is variable.

4. The apparatus of claim 1, wherein the first revascularization event is substantially simultaneous with a creation of the first created heartbeat.

5. The apparatus of claim 1, wherein the selected time is fixed to cause the first revascularization event to occur after a depolarization of the heart and before a repolarization of the heart.

6. The apparatus of claim 1, wherein the selected time is fixed to cause the first revascularization event to occur after an R wave produced by the heart and before a T wave produced by the heart.

7. The apparatus of claim 1, wherein the selected time is fixed to cause the first revascularization event to occur after the revascularization device has delivered energy to the heart to cause the first created heartbeat and before the first heartbeat.

8. The apparatus of claim 1 wherein the control circuit is configured to cause created heartbeats at a pace faster than a normal heartbeat.

9. The apparatus of claim 1, wherein the control circuit is configured to be coupled to a device for sensing heart function.

10. The apparatus of claim 9, wherein the control circuit is configured to cause created heartbeats at a pace faster than a normal heartbeat.

11. The apparatus of claim 9, wherein the device for sensing is a flow measurement device.

12. The apparatus of claim 9, wherein the device for sensing is a pressure measurement device.

13. The apparatus of claim 9, wherein the device for sensing is an electrocardiogram device.

14. The apparatus of claim 1, wherein the first revascularization event has a fixed duration.

15. The apparatus of claim 1, wherein the first revascularization event has a variable duration.

16. The apparatus of claim 1, wherein control circuit is configured to cause the revascularization device to cause multiple heartbeats at a selected rate.

17. The apparatus of claim 16, wherein the control circuit is configured to cause the revascularization device to cause multiple revascularization events in the heart.

18. The apparatus of claim 1, wherein the control circuit is configured to cause multiple events between heartbeats.

19. The apparatus of claim 1, wherein the revascularization device is configured for transmyocardial revascularization.

20. The apparatus of claim 1, wherein the revascularization device is an ultrasound energy delivery device.

21. The apparatus of claim 1, wherein the revascularization device is a mechanical cutter.

22. The apparatus of claim 1, wherein the revascularization device is a laser energy delivery device.

23. The apparatus of claim 1, further comprising a catheter coupled to the revascularization device for percutaneous use.

24. The apparatus of claim 1, wherein the revascularization device is configured for surgical use.

25. The apparatus of claim 1, wherein the revascularization device is configured for minimally invasive surgery (MIS) use.

26. An apparatus for treating a heart, the apparatus comprising:

a device for causing a first created heartbeat, wherein the device for causing the first created heartbeat comprises at least one of a laser energy delivery device, an ultrasound energy delivery device, a mechanical cutter, or a piercer; and wherein the device for causing the first created heartbeat is configured for creating a first revascularization event in the heart, the device being controllable to provide a first revascularization event to occur at a selected time in relation to the first created heartbeat.

27. The apparatus of claim 26, wherein the selected time is fixed to cause the first revascularization event to occur after a depolarization of the heart and before a repolarization of the heart.

28. The apparatus of claim 26, wherein the selected time is fixed to cause the first revascularization event to occur after an R wave produced by the heart and before a T wave produced by the heart.

29. The apparatus of claim 26 wherein the device for causing the first created heartbeat is configured to cause the heart to beat at pace faster than a normal heartbeat.

30. The apparatus of claim 26, wherein the device for causing the first heartbeat is configured to be coupled to a device for sensing heart function.

31. The apparatus of claim 26, wherein device for causing the first created heartbeat comprises a laser energy delivery device.

32. The apparatus of claim 26, wherein the device for causing the first created heartbeat comprises an ultrasound energy delivery device.

33. The apparatus of claim 26, wherein the revascularization device comprises a mechanical cutter.

34. The apparatus of claim 26, wherein the device for causing the first created heartbeat comprises a piercer.

35. The apparatus of claim 26, further comprising a catheter coupled to the device for causing the first created heartbeat for percutaneous use.

36. An apparatus for treating a heart by stimulating revascularization of the heart or creating channels in the heart, the apparatus comprising:

a laser; and a control circuit, coupled to the laser, adapted to cause the laser to cause a first created heartbeat and to cause the laser to create a first revascularization event in the heart at a selected time in relation to the first created heartbeat.

37. The apparatus of claim 36, wherein the selected time is fixed to cause the first revascularization event to occur after a depolarization of the heart and before a repolarization of the heart.

38. The apparatus of claim 36, wherein the selected time is fixed to cause the first revascularization event to occur after an R wave produced by the heart and before a T wave produced by the heart.

39. The apparatus of claim 36, wherein the control circuit is configured to cause the laser to cause created heartbeats at a rate faster than a normal heartbeat.

40. The apparatus of claim 36, wherein the control circuit is configured to be coupled to a device for sensing heart function.

41. The apparatus of claim 36, further comprising a catheter coupled to the revascularization device for percutaneous use.

* * * * *